United States Patent [19]

Ueda et al.

[11] Patent Number: 5,801,251
[45] Date of Patent: *Sep. 1, 1998

[54] PROCESS FOR CRYSTALLIZING $N^2$-((S)-1-ETHOXYCARBONYL-3-PHENYLPROPYL)-$N^6$-TRIFLUOROACETYL-L-LYSYL-L-PROLINE

[75] Inventors: Yasuyoshi Ueda, Himeji; Hajime Manabe, Takasago, both of Japan

[73] Assignee: Kanegafuchi Kagaku Kogyo Kabushiki Kaisha, Osaka, Japan

[*] Notice: The term of this patent shall not extend beyond the expiration date of Pat. No. 5,519,146.

[21] Appl. No.: 642,308

[22] Filed: May 3, 1996

Related U.S. Application Data

[62] Division of Ser. No. 295,649, Aug. 26, 1994, Pat. No. 5,519,146.

[30] Foreign Application Priority Data

Jan. 8, 1993 [JP] Japan ................. 2044/1993

[51] Int. Cl.⁶ .................................................. C07D 207/16
[52] U.S. Cl. ................................................... 548/533
[58] Field of Search ....................................... 548/533

[56] References Cited

U.S. PATENT DOCUMENTS

| | | |
|---|---|---|
| 4,687,840 | 8/1987 | Pang et al. ............ 548/333 X |
| 4,868,312 | 9/1989 | Maeda et al. ............ 548/333 |
| 5,227,497 | 7/1993 | Inoue et al. ............ 548/333 |
| 5,359,086 | 10/1994 | Merslavic et al. ............ 548/333 |
| 5,387,696 | 2/1995 | Kottenhahn et al. ............ 548/333 |
| 5,519,146 | 5/1996 | Ueda et al. ............ 548/533 |

FOREIGN PATENT DOCUMENTS

| | | |
|---|---|---|
| 0215335 | 3/1987 | European Pat. Off. . |
| 61-36297 | 2/1986 | Japan . |
| 62-135491 | 6/1987 | Japan . |
| 1-254651 | 10/1989 | Japan . |
| 5-201882 | 8/1993 | Japan . |
| WO95/07928 | 3/1995 | WIPO . |

OTHER PUBLICATIONS

International Search Report for International Appln. No. PCT/JP93/01909 mailed April 12, 1994.

*Primary Examiner*—Johann Richter
*Assistant Examiner*—Ebenezer Sackey
*Attorney, Agent, or Firm*—Varndell Legal Group

[57] ABSTRACT

A process for crystallizing $N^2$-((S)-1-ethoxycarbonyl-3-phenylpropyl)-$N^6$-trifluoroacetyl-L-lysyl-L-proline using one or a mixture of at least two kinds of compound having the general formula: $CR^1R^2R^3R^4$ as a crystallizing solvent, optionally with an auxiliary solvent which controls crystallization condition.

17 Claims, 3 Drawing Sheets

PROCESS FOR CRYSTALLIZING $N^2$-((S)-1-ETHOXYCARBONYL-3-PHENYLPROPYL)-$N^6$-TRIFLUOROACETYL-L-LYSYL-L-PROLINE

CROSS-REFERENCE TO RELATED APPLICATION

This application is a divisional application of U.S. Ser. No. 08/295,649, filed on Aug. 26, 1994, now U.S. Pat. No. 5,519,146.

TECHNICAL FIELD

The present invention relates to a process for crystallizing $N^2$-((S)-1-ethoxycarbonyl-3-phenylpropyl)-$N^6$-trifluoroacetyl-L-lysyl-L-proline which is useful as an intermediate for the preparation of an inhibitor of angiotensin converting enzyme (ACE), Lisinopril ($N^2$-((S)-1-carboxy-3-phenylpropyl)-L-lysyl-L-proline).

BACKGROUND ART $N^2$-((S)-1-ethoxycarbonyl-3-phenylpropyl)-$N^6$-trifluoroacetyl-L-lysyl-L-proline can be prepared by a method described in Japanese Unexamined Patent Publication No. 36297/1986, and the like. As a method for isolation and purification of thus obtained $N^2$-((S)-1-ethoxycarbonyl-3-phenylpropyl)-$N^6$-trifluoroacetyl-L-lysyl-L-proline, crystallizing method is extremely easy. In Japanese Unexamined Patent Publication No. 36297/1986, there is described a crystallizing method using methyl tert-butyl ether/ cyclohexane (650 ml/240 ml). Also, in Journal of Organic Chemistry, 53, p836–843 (1988), there is disclosed a crystallizing method using methyl tert-butyl ether/cyclohexane or methyl tert-butyl ether/hexanes ($C_6H_{14}$) (225 ml/85 ml cyclohexane). However, as to the methods using these solvents as crystallizing solvents, there are problems that the solvents are highly hazardous and that the crystal properties of the resulting $N^2$-((S)-1-ethoxycarbonyl-3-phenylpropyl)-$N^6$-trifluoroacetyl-L-lysyl-L-proline is unfavorable. Therefore these methods are not necessarily preferable. Due to the unfavorable crystal properties, solid-liquid separation takes long period and mother liquor cannot be sufficiently replaced when washing cake. Further, once obtained crystal easily melts or becomes oily (syrupy). So, during solid liquid separating step to drying step, there arise following problems. That is, the molten or oily state of some or almost of crystal results in unsuccessful separation and collection thereof. Also, the extreme difficulty of the removal of solvents from the obtained oily matter or molten matter, requires long period for drying step or results in stopping of drying step halfway.

Preliminary research of the present inventors for crystallizing solvents other than methyl tert-butyl ether/ cyclohexane or methyl tert-butyl ether/hexanes ($C_6H_{14}$) has shown problems that $N^2$-((S)-1-ethoxycarbonyl-3-phenylpropyl)-$N^6$-trifluoroacetyl-L-lysyl-L-proline is not crystallized or is obtained only in an oily state, or even if gelled matter is obtained, collection by filtration cannot be done due to unsuccessful crystallization. Thus it has been proved that the crystallization is an extremely difficult technical subject.

An object to be solved by the present invention is to find out solvents which enable the crystallization of $N^2$-((S)-1-ethoxycarbonyl-3-phenylpropyl)-$N^6$-trifluoroacetyl-L-lysyl-L-proline with favorable crystal properties, instead of methyl tert-butyl ether/cyclohexane or methyl tert-butyl ether/hexanes ($C_6H_{14}$).

DISCLOSURE OF THE INVENTION

As a result of continuous effort and earnest investigation of the present inventors with respect to solvents for crystallization of $N^2$-((S)-1-ethoxycarbonyl-3-phenylpropyl)-$N^6$-trifluoroacetyl-L-lysyl-L-proline, it has been found that solvents which enable the crystallization with favorable crystal properties have molecular structures quite similar to each other.

That is, the present invention relates to a process for crystallizing $N^2$-((S)-1-ethoxycarbonyl-3-phenylpropyl)-$N^6$-trifluoroacetyl-L-lysyl-L-proline by using one or a mixture of at least two kinds of compound having the general formula:

wherein $R^1$ is chlorine atom, bromine atom, methoxy group, acetyl group, acetoxy group, chloromethyl group or phenyl group; $R^2$ is hydrogen atom, chlorine atom, bromine atom, methyl group, ethyl group or methoxy group; $R^3$ is chlorine atom, bromine atom, methyl group or methoxy group; $R^4$ is chlorine atom, bromine atom, methyl group, ethyl group or methoxy group; provided that the combination wherein $R^1$ is methoxy group and $R^2$, $R^3$ and $R^4$ are methyl group is excluded, as a crystallizing solvent.

The present invention also relates to a process for crystallizing $N^2$-((S)-1-ethoxycarbonyl-3-phenylpropyl)-$N^6$-trifluoroacetyl-L-lysyl-L-proline by using a mixture of methyl tert-butyl ether and one or more of compound having the general formula:

wherein $R^1$ is chlorine atom, bromine atom, methoxy group, acetyl group, acetoxy group, chloromethyl group or phenyl group; $R^2$ is hydrogen atom, chlorine atom, bromine atom, methyl group, ethyl group or methoxy group; $R^3$ is chlorine atom, bromine atom, methyl group or methoxy group; $R^4$ is chlorine atom, bromine atom, methyl group, ethyl group or methoxy group; provided that the combination wherein $R^1$ is methoxy group and $R^2$, $R^3$ and $R^4$ are methyl group is excluded, as a crystallizing solvent.

The present invention also relates to a process for crystallizing $N^2$-((S)-1-ethoxycarbonyl-3-phenylpropyl)-$N^6$-trifluoroacetyl-L-lysyl-L-proline, wherein an auxiliary solvent for controlling crystallizing condition such as solubility, crystallization concentration, yield and crystal properties of $N^2$-((S)-1-ethoxycarbonyl-3-phenylpropyl)-$N^6$-trifluoroacetyl-L-lysyl-L-proline, is used together with the above-mentioned crystallizing solvent.

The present invention also relates to a process for crystallizing $N^2$-((S)-1-ethoxycarbonyl-3-phenylpropyl)-$N^6$-trifluoroacetyl-L-lysyl-L-proline, wherein methyl tert-butyl ether is used as the crystallizing solvent, and methylcyclohexane is used as the auxiliary solvent for controlling crystallizing condition such as solubility, crystallization concentration, yield and crystal properties of $N^2$-((S)-1-ethoxycarbonyl-3-phenylpropyl)-$N^6$-trifluoroacetyl-L-lysyl-L-proline.

BEST MODE FOR CARRYING OUT THE INVENTION

As examples of the compound as the crystallizing solvent usable in the process of the present invention, which have the general formula:

$$CR^1R^2R^3R^4$$

wherein $R^1$ is chlorine atom, bromine atom, methoxy group, acetyl group, acetoxy group, chloromethyl group or phenyl group; $R^2$ is hydrogen atom, chlorine atom, bromine atom, methyl group, ethyl group or methoxy group; $R^3$ is chlorine atom, bromine atom, methyl group or methoxy group; $R^4$ is chlorine atom, bromine atom, methyl group, ethyl group or methoxy group; provided that the combination wherein $R^1$ is methoxy group and $R^2$, $R^3$ and $R^4$ are methyl group is excluded, there can be exemplified methyl tert-butyl ketone, tert-butylbenzene, phenyltrichloromethane, carbon tetrabromide, isopropyl acetate, tert-butyl acetate, 2,2-dimethoxypropane, trimethyl orthoacetate, tetramethyl orthocarbonate, isobutyl chloride, tert-butyl chloride, 2,2-dichloropropane, 1,1,1-trichloroethane, carbon tetrachloride, 1,1,2-trichloroethane, neopentyl chloride, 2,2-dichlorobutane, bromotrichloromethane, and the like. These may be used as a mixture of at least two kinds of them. Also, a mixture of one or more of them with methyl tert-butyl ether (which corresponds to the combination that $R^1$ is methoxy group, $R^2$, $R^3$ and $R^4$ are methyl group, in the general formula $CR^1R^2R^3R^4$) may be used.

The above-mentioned crystallizing solvent usable in the present invention has a molecular structure wherein a basic structure, namely, $C(CH_3)_4$ (neopentane), $CCl_4$ (carbon tetrachloride), $CBr_4$ (carbon tetrabromide) or $C(OCH_3)_4$ (tetramethyl orthocarbonate) (all of them consisting of central carbon atom and four substituents which have relatively similar size (methyl groups, chlorine atoms, bromine atoms or methoxy groups)) is substituted so that the structure has at least one chlorine atom, bromine atom, methoxy group, acetyl group, acetoxy group, chloromethyl group or phenyl group. Thus, the above-mentioned crystallizing solvent has a similar molecular size to that of the basic structure as a whole.

From the above-mentioned fact, it can be conjectured that the molecular form and the presence of suitable substituents of a solvent to be used for the crystallization are significant for the crystallization of $N^2$-((S)-1-ethoxycarbonyl-3-phenylpropyl)-$N^6$-trifluoroacetyl-L-lysyl-L-proline which is originally hard to be crystallized. That is, it can be considered that when the molecular form and the substituents of a solvent are maintained within a suitable range, there arises some interaction between $N^2$-((S)-1-ethoxycarbonyl-3-phenylpropyl)-$N^6$-trifluoroacetyl-L-lysyl-L-proline and the solvent, which interaction enables the crystallization.

Thus, $N^2$-((S)-1-ethoxycarbonyl-3-phenylpropyl)-$N^6$-trifluoroacetyl-L-lysyl-L-proline easily interacts with the above-mentioned various kinds of atoms or substituents. On the other hand, a solvent which does not have the above-mentioned molecular form, or atoms or substituents, is not suitable as the crystallizing solvent. For example, an aliphatic hydrocarbon (such as n-hexane, n-heptane, neopentane, cyclohexane or methylcyclohexane) does not cause such interaction and the solubility therein is extremely low. Therefore, such solvent alone cannot be the crystallizing solvent.

In order to confirm the above-mentioned, the present inventors, at first, crystallized $N^2$-((S)-1-ethoxycarbonyl-3-phenylpropyl)-$N^6$-trifluoroacetyl-L-lysyl-L-proline by using the above-mentioned crystallizing solvent usable in the present invention and detected the amount of the solvent present inside the obtained crystal. As a result, the solvent in an amount of approximately 1 to 100 mole %, which varies depending on the kind of the solvent, was found per $N^2$-((S)-1-ethoxycarbonyl-3-phenylpropyl)-$N^6$-trifluoroacetyl-L-lysyl-L-proline. Further, it was recognized that the amount of the solvent present inside the crystal is affected by the molecular form or the bulkiness of the solvent molecule or the kind of substituents present therein, and when the bulkiness or the flexibility of the solvent molecule is large, the amount of the solvent present inside the crystal (mole %) tends to be lower.

Moreover, in order to confirm the interaction of the above-mentioned solvent molecules and $N^2$-((S)-1-ethoxycarbonyl-3-phenylpropyl)-$N^6$-trifluoroacetyl-L-lysyl-L-proline molecule, $N^2$-((S)-1-ethoxycarbonyl-3-phenylpropyl)-$N^6$-trifluoroacetyl-L-lysyl-L-proline was crystallized by using $CH_3CCl_3$ (1,1,1-trichloroethane) and FT-IR of the obtained $N^2$-((S)-1-ethoxycarbonyl-3-phenylpropyl)-$N^6$-trifluoroacetyl-L-lysyl-L-proline was measured with respect to the samples on various drying times. As a result, it was shown that the solvent molecule present inside the crystal interacts with at least trifluoroacetyl-moiety in $N^2$-((S)-1-ethoxycarbonyl-3-phenylpropyl)-$N^6$-trifluoroacetyl-L-lysyl-L-proline molecule.

Therefore, it is recognized that in order to carry out the crystallization of $N^2$-((S)-1-ethoxycarbonyl-3-phenylpropyl)-$N^6$-trifluoroacetyl-L-lysyl-L-proline, groups having a flexibility such as trifluoroacetylaminobutyl or groups which do not suitably serve for crystallization in $N^2$-((S)-1-ethoxycarbonyl-3-phenylpropyl)-$N^6$-trifluoroacetyl-L-lysyl-L-proline molecule, are required to be maintained in a state that crystallization can be done. Therefore it is recognized to be a significant requirement that there should be used a compound whose molecular form and substituents are within a suitable range, as the crystallizing solvent. Thus it was found that the solvent present inside crystal is largely related to the state of the crystallization and crystal properties. The above-mentioned crystallizing solvents satisfy this requirement.

Control for crystallizing conditions such as solubility, crystallization concentration, yield and crystal properties of $N^2$-((S)-1-ethoxycarbonyl-3-phenylpropyl)-$N^6$-trifluoroacetyl-L-lysyl-L-proline is, however, naturally sometimes unsuitable. In such case, a suitable amount of an auxiliary solvent can be added to the above-mentioned crystallizing solvent for controlling the above-mentioned condition. As such auxiliary solvent, there can be exemplified diethyl ketone, dioxane, ethyl acetate, nitromethane, methylene chloride, tert-butanol, benzene, n-hexane, cyclohexane, methylcyclohexane, and the like.

Particularly, there is preferably employed a method wherein crystallization concentration is increased by improving the solubility to some extent, using methylene chloride or ethyl acetate, or a method wherein yield and crystal properties are improved by using methylcyclohexane. In case of using, for example, methylcyclohexane as the auxiliary solvent, due to the effect thereof on phase transition property and amount of solvent present inside crystal, operability in drying step is more excellent and crystal which hardly melts can be obtained, compared with the case of using cyclohexane, while the effects on a solvent for crystallizing $N^2$-((S)- 1-ethoxycarbonyl-3-phenylpropyl)-$N^6$-trifluoroacetyl-L-lysyl-L-proline are similar to each other.

These auxiliary solvents can be effectively used together with a crystallizing solvent in a preferred ratio, according to characteristic of each auxiliary solvent based on known properties such as melting point, boiling point, vapor pressure property and phase transition, the amount of solvent present inside crystal mentioned above, and effect on solubility of $N^2$-((S)-1-ethoxycarbonyl-3-phenylpropyl)-$N^6$-trifluoroacetyl-L-lysyl-L-proline.

Now, it has now been found that the action mechanism of methyl tert-butyl ether, which has been known as an excellent crystallizing solvent for $N^2$-((S)-1-ethoxycarbonyl-3-phenylpropyl)-$N^6$-trifluoroacetyl-L-lysyl-L-proline, is also based on its molecular structure which corresponds to the crystallizing solvent of the present invention. Therefore, it can be also combined with an auxiliary solvent to control the crystallization condition of $N^2$-((S)-1-ethoxycarbonyl-3-phenylpropyl)-$N^6$-trifluoroacetyl-L-lysyl-L-proline. Particularly, in case of using methyl tert-butyl ether together with methylcyclohexane as the auxiliary solvent, the characteristic of methylcyclohexane as mentioned above can be shown, compared with the combination with cyclohexane described in Japanese Unexamined Patent Publication No. 36297/1986. In this case, the ratio of methyl tert-butyl ether and methylcyclohexane can be substantially the same degree ratio as in the combination with cyclohexane described in Japanese Unexamined Patent Publication No. 36297/1986. The weight ratio of methyl tert-butyl ether/methylcyclohexane is, however, practically 1/1 to 1/0.1, preferably 1/0.7 to 1/0.2, more preferably 1/0.4 to 1/0.25, at the end point of the crystallization. When the ratio of methyl tert-butyl ether/methylcyclohexane is at most 1/1, there deposit impurities and the quality of the resulting crystal deteriorates, or there tends to be collected oily matter or crystal having worse crystal properties. When the ratio is larger than 1/0.1, the yield lowers or melting preventing effect for crystal is low. Thus such ratio is not preferable.

As a crystallizing method using the above-mentioned compound as a solvent, there can be employed a usual crystallizing method such as cooling crystallization, concentrating crystallization or a crystallizing method wherein a solution comprising the other solvents is replaced with solution comprising the above-mentioned compounds. On the crystallization, seed crystal can be added. In order to improve the crystal properties, handling property or yield of $N^2$-((S)-1-ethoxycarbonyl-3-phenylpropyl)-$N^6$-trifluoroacetyl-L-lysyl-L-proline crystal to be obtained, mixture solvent of at least two kinds can be used, or a suitable amount of an auxiliary solvent such as n-hexane, cyclohexane or methylcyclohexane can be added previously or during the crystallization. In case that the crystallization cannot be easily carried out owing to the effect of coexistent impurities, it is preferably employed that firstly the crystallization is carried out by using only a crystallizing solvent, and then an auxiliary solvent is successively added.

Thus obtained $N^2$-((S)-1-ethoxycarbonyl-3-phenylpropyl)-$N^6$-trifluoroacetyl-L-lysyl-L-proline crystal can be subjected to a usual solid-liquid separation, cake washing and then drying. As a method for solid-liquid separation, there can be employed a usual method such as pressure filtration, filtration under reduced pressure or centrifugation. As a drying method, drying under reduced pressure (vacuum drying) at a low temperature of about 20° C. to about 50° C. is preferably employed from the viewpoint of suppression of melting or becoming oily. In order to improve the crystal properties or the handling property of wet crystal, the wet crystal can be washed or replaced with the compounds usable in carrying out the present invention.

Hereinafter, the present invention is explained by means of Examples and Reference Examples. However, it should not be recognized that the present invention is limited to these.

EXAMPLE 1

$N^2$-((S)-1-ethoxycarbonyl-3-phenylpropyl)-$N^6$-trifluoroacetyl-L-lysyl-L-proline was dissolved with heating in a concentration of at most 100 w/v % into a compound in Table 1 as a solvent, to give each transparent solution. The resulting solution is cooled to room temperature and observed the presence of crystal deposition.

TABLE 1

| No. | Compound used as a solvent | Presence of crystal deposition |
| --- | --- | --- |
| 1 | Water | − |
| 2 | Methanol | − |
| 3 | Ethanol | − |
| 4 | Isopropanol | − |
| 5 | tert-butanol | − |
| 6 | tert-pentyl alcohol | − |
| 7 | neopentyl alcohol | − |
| 8 | acetonitrile | − |
| 9 | propionitrile | − |
| 10 | acrylonitrile | − |
| 11 | acetone | − |
| 12 | methyl ethyl ketone | − |
| 13 | diethyl ketone | − |
| 14 | methyl n-propyl ketone | − |
| 15 | methyl n-butyl ketone | − |
| 16 | methyl isobutyl ketone | − |
| 17 | methyl tert-butyl ketone | + |
| 18 | acetophenone | − |
| 19 | benzene | − |
| 20 | toluene | − |
| 21 | xylene | − |
| 22 | n-butylbenzene | − |
| 23 | sec-butylbenzene | − |
| 24 | tert-butylbenzene | + |
| 25 | phenyltrichloromethane | + |
| 26 | thiophen | − |
| 27 | methyl acetate | − |
| 28 | ethyl acetate | − |
| 29 | isopropyl acetate | + |
| 30 | isobutyl acetate | − |
| 31 | tert-butyl acetate | − |
| 32 | γ-butyrolactane | − |
| 33 | nitromethane | − |
| 34 | nitroethane | − |
| 35 | diethyl ether | − |
| 36 | dioxane | − |
| 37 | anisole | − |
| 38 | methyl tert-butyl ether | + |
| 39 | 2,2-dimethoxypropane | + |
| 40 | trimethyl orthoacetate | + (slight crystallization) |
| 41 | tetramethyl orthocarbonate | + |
| 42 | formic acid | − |
| 43 | acetic acid | − |
| 44 | n-hexane | − |
| 45 | cyclohexane | − |
| 46 | methylcyclohexane | − |
| 47 | neopentane | − |
| 48 | methylene chloride | − |
| 49 | 1,2-dichloroethane | − |
| 50 | n-butyl chloride | − |
| 51 | isobutyl chloride | + |
| 52 | tert-butyl chloride | + |
| 53 | 2,2-dichloropropane | + |
| 54 | 1,1,1-trichloroethane | + |
| 55 | carbon tetrachloride | + |

TABLE 1-continued

| No. | Compound used as a solvent | Presence of crystal deposition |
|---|---|---|
| 56 | 1,1,2-trichloroethane | + |
| 57 | neopentyl chloride | + |
| 58 | 2,2-dichlorobutane | + |
| 59 | bromotrichloromethane | + |
| 60 | dimethylformamide | − |
| 61 | dimethylsulfoxide | − |

EXAMPLE 2

Into 100 ml of 1,1,1-trichloroethane was dissolved 12 g of $N^2$-((S)-1-ethoxycarbonyl-3-phenylpropyl)-$N^6$-trifluoroacetyl-L-lysyl-L-proline with heating. Then the solution was cooled to room temperature and the deposited crystal was collected by filtration. The obtained crystal was washed with 1,1,1-trichloroethane and dried under reduced pressure, to give about 9 g of the crystal. The melting point of the dry crystal was 78° C.

EXAMPLE 3

A mixture of 15 g of $N^2$-((S)-1-ethoxycarbonyl-3-phenylpropyl)-$N^6$-trifluoroacetyl-L-lysyl-L-proline, 31 g of carbon tetrachloride, and 20 g of isopropyl acetate was dissolved with heating, followed by filtering off an insoluble matter. After cooling with ice, the deposited crystal was collected by filtration and sufficiently washed with n-heptane. The resulting crystal was about 15 g.

EXAMPLE 4

A mixture of 15 g of $N^2$-((S)-1-ethoxycarbonyl-3-phenylpropyl)-$N^6$-trifluoroacetyl-L-lysyl-L-proline, 31 g of carbon tetrachloride and 17 g of methyl tert-butyl ether was dissolved under heating, followed by filtering off an insoluble matter. After cooling with ice, the deposited crystal was collected by filtration and washed sufficiently with cyclohexane. The resulting crystal was 12 g.

EXAMPLE 5

A mixture of 15 g of $N^2$-((S)-1-ethoxycarbonyl-3-phenylpropyl)-$N^6$-trifluoroacetyl-L-lysyl-L-proline, 64 g of carbon tetrabromide and 17 g of methyl tert-butyl ether was dissolved under heating, followed by filtering off an insoluble matter. After cooling with ice, the deposited crystal was collected by filtration and washed sufficiently with cyclohexane. The resulting crystal was 10 g.

EXAMPLE 6

A mixture of 20 g of $N^2$-((S)-1-ethoxycarbonyl-3-phenylpropyl)-$N^6$-trifluoroacetyl-L-lysyl-L-proline, 14 g of 1,1,1-trichloroethane and 8 g of diethyl ketone was dissolved with heating, followed by filtering off an insoluble matter. The resulting solution was cooled to deposit crystal. The deposited crystal was 17 g.

EXAMPLE 7

A mixture of 30 g of $N^2$-((S)-1-ethoxycarbonyl-3-phenylpropyl)-$N^6$-trifluoroacetyl-L-lysyl-L-proline, 10 g of carbon tetrabromide and 8 g of diethyl ketone was dissolved with heating, followed by filtering off an insoluble matter. The resulting solution was cooled to deposit crystal. The deposited crystal was 23 g.

EXAMPLE 8

A mixture of 15 g of $N^2$-((S)-1-ethoxycarbonyl-3-phenylpropyl)-$N^6$-trifluoroacetyl-L-lysyl-L-proline, 27 g of 1,1,1-trichloroethane and 17 g of methyl tert-butyl ether was dissolved with heating, followed by filtering off an insoluble matter. Then the resulting solution was cooled with ice to deposit crystal. Thereto was added 10 g of methylcyclohexane. The obtained crystal was collected by filtration and washed with a mixed solvent of 8 g of 1,1,1-trichloroethane, 5 g of methyl tert-butyl ether and 3 g of methylcyclohexane, then with 10 g of methylcyclohexane. The obtained crystal was 12 g. The melting point of the dry crystal was 78° C.

EXAMPLE 9

A mixture of 3 g of $N^2$-((S)-1-ethoxycarbonyl-3-phenylpropyl)-$N^6$-trifluoroacetyl-L-lysyl-L-proline, 3 g of methylcyclohexane and 12 g of methyl tert-butyl ether was dissolved with heating, followed by filtering off an insoluble matter. The resulting solution was cooled to deposit crystal. The deposited crystal was about 2 g.

EXAMPLE 10

A mixture of 6 g of $N^2$-((S)-1-ethoxycarbonyl-3-phenylpropyl)-$N^6$-trifluoroacetyl-L-lysyl-L-proline and 20 g of methyl tert-butyl ether was dissolved with heating, followed by filtering off an insoluble matter. Then thereto was added seed crystal, and the mixture was cooled to deposit crystal. After stirring overnight, thereto was added dropwise 13 g of methylcyclohexane, followed by cooling with ice. After filtration, the residue was washed with cooled methyl tert-butyl ether/methylcyclohexane (weight ratio 5:2). The deposited crystal was about 6 g.

REFERENCE EXAMPLE 1

Each crystal was collected by filtering the suspension obtained in Example 1 with No. 38, 39 or 41. Then the crystal was sufficiently washed with n-hexane. The amount of solvent present inside the crystal (mole % of the solvent used for the crystallization per $N^2$-((S)-1-ethoxycarbonyl-3-phenylpropyl)-$N^6$-trifluoroacetyl-L-lysyl-L-proline, hereinafter the same) was determined with respect to the above-mentioned sample. The results are shown in Table 2.

TABLE 2

| No. | Amount of solvent present inside crystal (mole %) |
|---|---|
| 38 | 57 |
| 39 | 25 |
| 41 | 14 |

REFERENCE EXAMPLE 2

Each crystal was collected by filtering the suspension obtained in Example 1 with No. 52, 53, 54 or 55. Then the crystal was sufficiently washed with n-hexane. The amount of solvent present inside crystal was determined with respect to the above-mentioned sample. The results are shown in Table 3.

TABLE 3

| No. | Amount of solvent present inside crystal (mole %) |
|---|---|
| 52 | 48 |
| 53 | 69 |
| 54 | 66 |
| 55 | 54 |

REFERENCE EXAMPLE 3

The amount of solvent present inside crystal was determined with respect to the sample obtained in Example 3. There were found 48 mole % of carbon tetrachloride and 6 mole % of isopropyl acetate.

REFERENCE EXAMPLE 4

The amount of solvent present inside crystal was determined with respect to the sample obtained in Example 4. There were found 50 mole % of carbon tetrachloride and 31 mole % of methyl tert-butyl ether.

REFERENCE EXAMPLE 5

The amount of solvent present inside crystal was determined with respect to the sample obtained in Example 5. There were found 70 mole % of carbon tetrabromide and 23 mole % of methyl tert-butyl ether.

REFERENCE EXAMPLE 6

The amount of solvent present inside crystal was determined with respect to the sample obtained in Example 9. There were found 55 mole % of methyl tert-butyl ether and 22 mole % of methylcyclohexane. The wet crystal was vacuum dried at room temperature, to give the dry crystal having a melting point of 78° C.

REFERENCE EXAMPLE 7

A mixture of 6 g of $N^2$-((S)-1-ethoxycarbonyl-3-phenylpropyl)-$N^6$-trifluoroacetyl-L-lysyl-L-proline and 20 g of methyl tert-butyl ether was dissolved with heating, followed by filtering off an insoluble matter. Then thereto was added seed crystal, and the mixture was cooled to deposit crystal. After stirring overnight, thereto was added dropwise 8 g of cyclohexane, followed by cooling with ice. After the filtration, the residue was washed with cooled methyl tert-butyl ether/cyclohexane (weight ratio 5:2). The deposited crystal was about 6 g. The amount of solvent present inside crystal was determined and there were found 74 mole % of methyl tert-butyl ether and 18 mole % of cyclohexane. The wet crystal was vacuum dried at room temperature, to give the dry crystal having a melting point of 77° C. With respect to the wet crystal which was allowed to stand for 8 hours in an atmosphere at 20° C., there was observed a partial melting thereof.

REFERENCE EXAMPLE 8

A mixture of 6 g $N^2$-((S)-1-ethoxycarbonyl-3-phenylpropyl)-$N^6$-trifluoroacetyl-L-lysyl-L-proline and 20 g of methyl tert-butyl ether was dissolved with heating, followed by filtering off an insoluble matter. Then thereto was added seed crystal, and the mixture was cooled to deposit crystal. After stirring overnight, thereto was added dropwise 8 g of n-hexane, followed by cooling with ice. After the filtration, the residue was washed with cooled methyl tert-butyl ether/n-hexane (weight ratio 5:2). However, the contractibility of cake was large and therefore the washing operability was worse. The deposited crystal, of which deposited amount was about 6 g, seems transparent. The amount of solvent present inside crystal was determined. As a result, 56 mole % of methyl tert-butyl ether was detected, but n-hexane was not detected. The wet crystal, which easily melts, was immediately vacuum dried at room temperature, to give the dry crystal having a melting point of 74° C.

REFERENCE EXAMPLE 9

The amount of solvent present inside crystal was determined with respect to the sample obtained in Example 10. There were found 56 mole % of methyl tert-butyl ether and 16 mole % of methylcyclohexane. The wet crystal was vacuum dried at room temperature, to give the dry crystal having a melting point of 78° C. With respect to the wet crystal which was allowed to stand for 24 hours in an atmosphere at 20° C., there was not observed any melting indication.

REFERENCE EXAMPLE 10

A mixture of 3 g of $N^2$-((S)-1-ethoxycarbonyl-3-phenylpropyl)-$N^6$-trifluoroacetyl-L-lysyl-L-proline, 17 g of methylcyclohexane and 12 g of methyl tert-butyl ether was dissolved with heating, followed by filtering off an insoluble matter. The resulting solution was cooled to give an oily matter.

REFERENCE EXAMPLE 11

Into 30 ml of ethanol was dissolved 10 g of $N^2$-((S)-1-ethoxycarbonyl-3-phenylpropyl)-$N^6$-trifluoroacetyl-L-lysyl-L-proline. To this solution was added gradually cyclohexane, to give an oily matter.

REFERENCE EXAMPLE 12

Into 30 ml of methylene chloride was dissolved 10 g of $N^2$-((S)-1-ethoxycarbonyl-3-phenylpropyl)-$N^6$-trifluoroacetyl-L-lysyl-L-proline. To this solution was added gradually cyclohexane, to give an oily matter.

REFERENCE EXAMPLE 13

Figure 1:
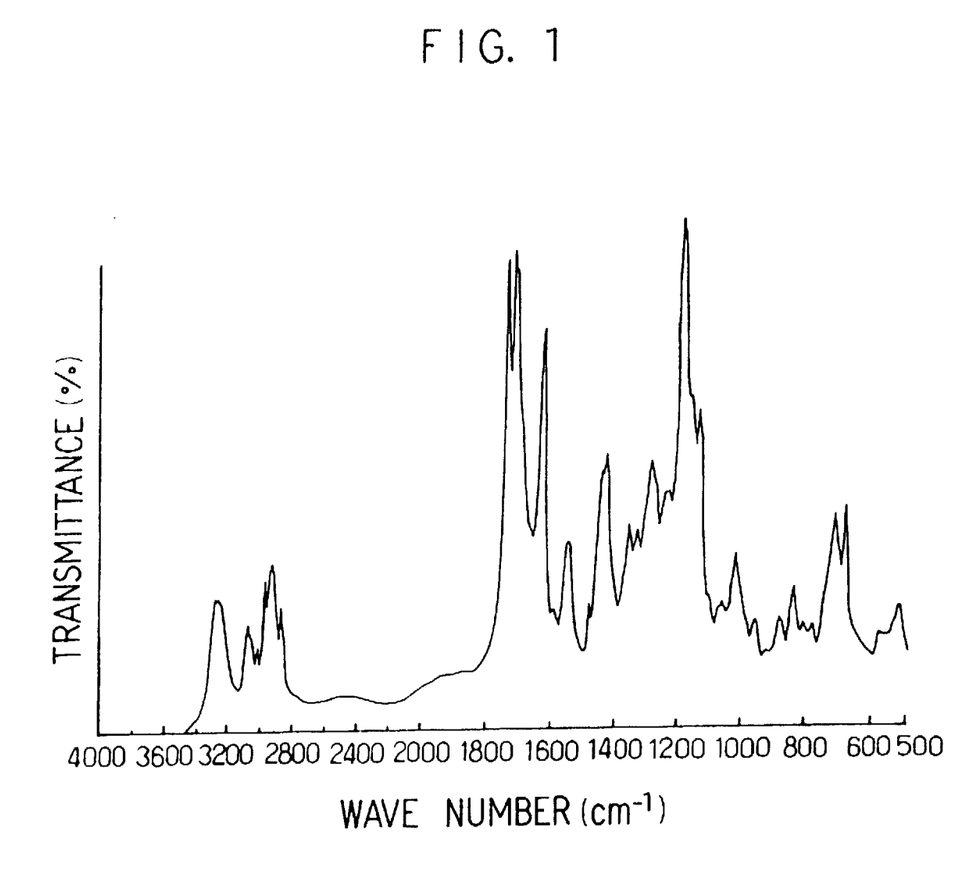
FIG. 1 is a chart showing the result of FT-IR measurement with respect to a sample containing 1 wt % of 1,1,1-trichloroethane in Reference Example 13.
Figure 2:
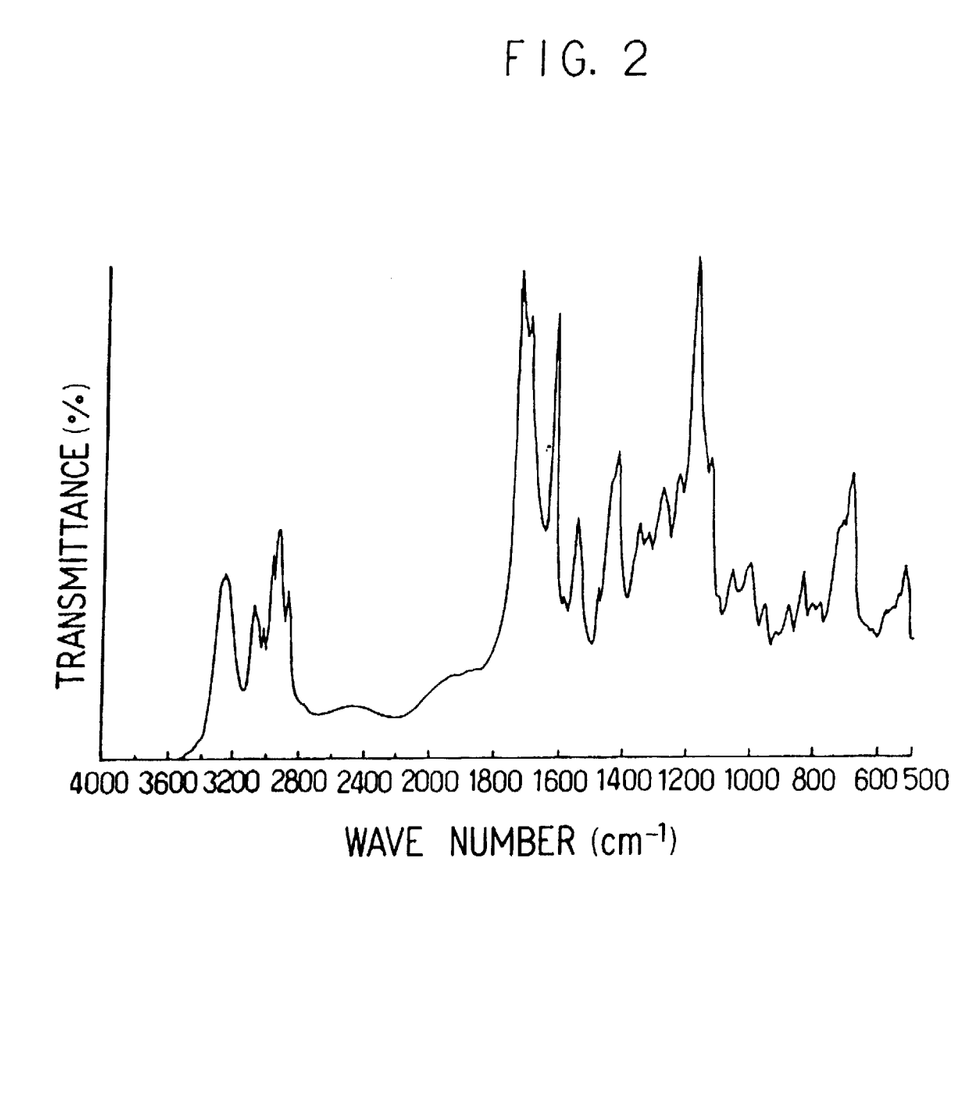
FIG. 2 is a chart showing the result of FT-IR measurement with respect to a sample containing 5 wt % of 1,1,1-trichloroethane in Reference Example 13.
Figure 3:
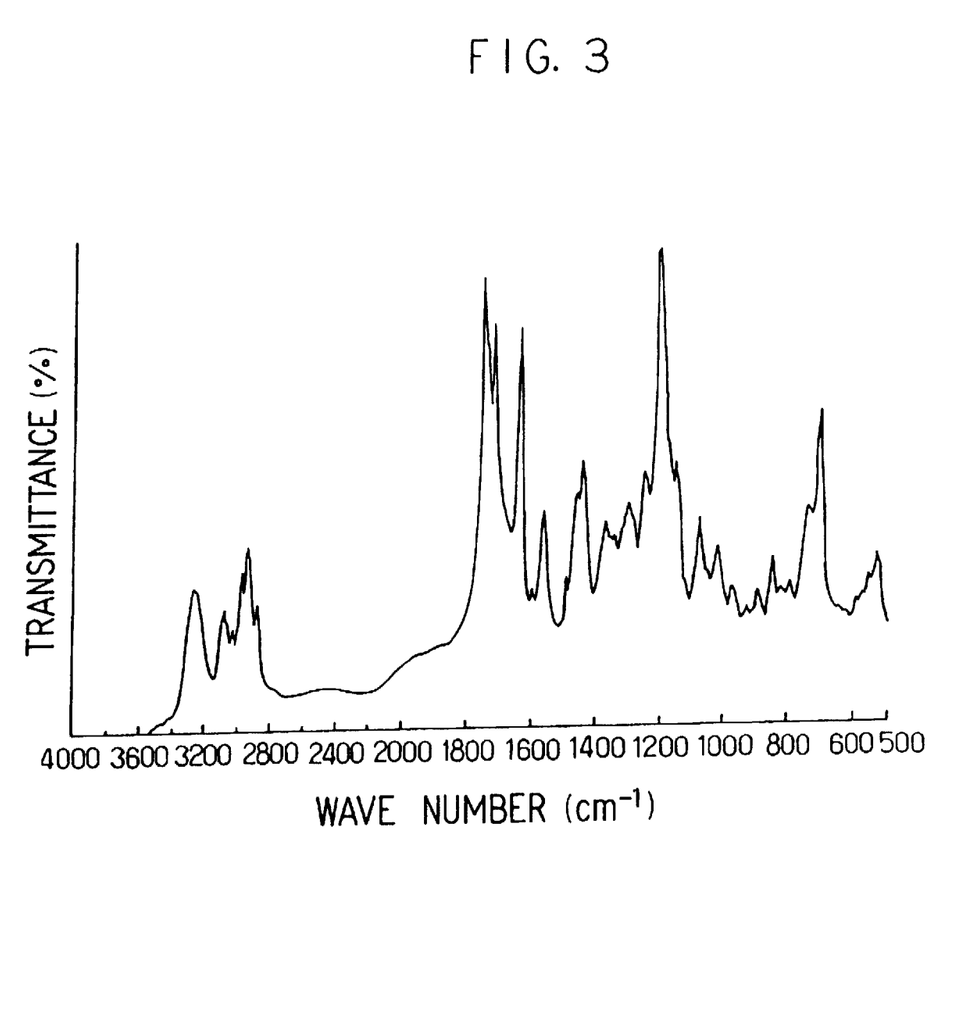
FIG. 3 is a chart showing the result of FT-IR measurement with respect to a sample containing 15 wt % of 1,1,1-trichloroethane in Reference Example 13.

FT-IR was measured with respect to samples in Example 2 obtained on various drying times. The results of FT-IR measurement are shown in FIG. 1 to FIG. 3.

Apparatus:

FTS-15E/D (trade name, made by Bio Rad Digilab, USA)
Attached Apparatus:
Diffuse reflectance spectrometer (trade name, made by Spectra tech, USA)
(Condition)
Light source: Special ceramics
Detector: MCT
Resolution: 4 cm$^{-1}$
Integrating times: 500 times
Sample dispersing medium: none As a result, the absorption peaks of each sample around at 3300 cm$^{-1}$ and 3100 cm$^{-1}$ were found at positions as shown in Table 4.

TABLE 4

| Content of 1,1,1-trichloroethane (wt %) | Position of absorption peak around 3300 cm⁻¹ (cm⁻¹) | Position of absorption peak around 3100 cm⁻¹ (cm⁻¹) |
|---|---|---|
| 1 | 3284.8<br>3265.5<br>3261.6 | 3088.0 |
| 5 | 3265.5<br>3252.0 | 3088.3 |
| 15 | 3273.2<br>3267.1 | 3090.0<br>3068.4 |

As clearly shown in FIG. 1 to FIG. 3, there were observed changes in the intensity of peak at 1724.4 cm$^{-1}$.

From the above-mentioned, it can be considered that the solvent interacts with the substrate, namely N$^2$-((S)-1-ethoxycarbonyl-3-phenylpropyl)-N$^6$-trifluoroacetyl-L-lysyl-L-proline, and that this interaction participates in the crystallization.

INDUSTRIAL APPLICABILITY

According to the present invention, N$^2$-((S)-1-ethoxycarbonyl-3-phenylpropyl)-N$^6$-trifluoroacetyl-L-lysyl-L-proline, which is very hard to be crystallized, can be stably obtained as a crystal with favorable crystal properties.

We claim:

1. A process for crystallizing N$^2$((S)-1-ethoxycarbonyl-3-phenylpropyl)-N$^6$-trifluoroacetyl-L-lysyl-L-proline which comprises first crystallizing said N$^2$-((S)-1-ethoxycarbonyl-3-phenylpropyl)-N$^6$-trifluoroacetyl-L-lysyl-L-proline from a solution of said N$^2$-((S)-1-ethoxycarbonyl-3-phenylpropyl)-N$^6$-trifluoroacetyl-L-lysyl-L-proline where a sufficient amount of at least one compound is used as a solvent, and then completing crystallization by successively adding a sufficient amount of auxiliary solvent for controlling crystallizing conditions, said compound having a property that said N$^2$-((S)-1-ethoxycarbonyl-3-phenylpropyl)-N$^6$-trifluoroacetyl-L-lysyl-L-proline can be crystallized from said solution therewith and having the general formula:

CR$^1$R$^2$R$^3$R$^4$ wherein R$^1$ is chlorine atom, bromine atom, methoxy group, acetyl group, acetoxy group, chloromethyl group or phenyl group; R$^2$ is hydrogen atom, chlorine atom, bromine atom, methyl group, ethyl group or methoxy group; R$^3$ is chlorine atom, bromine atom, methyl group or methoxy group; R$^4$ is chlorine atom, bromine atom, methyl group or methoxy group; provided that the combination, and wherein R$^1$ is methoxy group and R$^3$ and R$^4$ are methyl group is excluded.

2. The process for crystallizing as set forth in claim 1, wherein said compound is selected from the group consisting of methyl tert-butyl ketone, tert-butylbenzene, phenyltrichloromethane, carbon tetrabromide, isopropyl acetate, tert-butyl acetate, 2,2-dimethoxypropane, trimethyl orthoacetate, tetramethyl orthocarbonate, isobutyl chloride, tert-butyl chloride, 2,2-dichloropropane, 1,1,1-trichloroethane, carbon tetrachloride, 1,1,2-trichloroethane, neopentyl chloride, 2,2-dichlorobutane and bromotrichloromethane.

3. The process for crystallizing as set forth in claim 1, wherein said auxiliary solvent is selected from the group consisting of n-hexane, cyclohexane and methylcyclohexane.

4. The process for crystallizing as set forth in claim 2, wherein said auxiliary solvent is selected from the group consisting of n-hexane, cyclohexane and methylcyclohexane.

5. The process for crystallizing as set forth in claim 1, wherein said solvent consists of methyl tert-butyl ether and at least one of said compound.

6. The process for crystallizing of claim 2, wherein said solvent consists of methyl tert-butyl ether and at least one of said compound.

7. The process for crystallizing as set forth in claim 3, wherein said solvent consists of methyl tert-butyl ether and at least one of said compound.

8. A process for crystallizing N$^2$(S)-1-ethoxycarbonyl-3-phenylpropyl)-N$^6$-trifluoroacetyl-L-lysyl-L-proline, which comprises providing said N$^2$-((S)-1-ethoxycarbonyl-3-phenylpropyl)-N$^6$-trifluoroacetyl-L-lysyl-L-proline in a solution with a first solvent, replacing at least a portion of said first solvent with a compound and crystallizing N$^2$-((S)-1-ethoxycarbonyl-3-phenylpropyl)-N$^6$-trifluoroacetyl-L-lysyl-L-proline from the resultant replaced solution of N$^2$-((S)-1-ethoxycarbonyl-3-phenylpropyl)-N$^6$-trifluoroacetyl-L-lysyl-L-proline, said compound being different than said first solvent and having a property that said N$^2$-((S)-1-ethoxycarbonyl-3 -phenylpropyl)-N$^6$-trifluoroacetyl-L-lysyl-L-proline can be crystallized from said solution therewith and having the general formula:

CR$^1$R$^2$R$^3$R$^4$ wherein R$^1$ is chlorine atom, bromine atom, methoxy group, acetyl group, acetoxy group, chloromethyl group or phenyl group; R$^2$ is hydrogen atom, chlorine atom, bromine atom, methyl group, ethyl group or methoxy group; R$^3$ is chlorine atom, bromine atom, methyl group or methoxy group; R$^4$ is chlorine atom, bromine atom, methyl group or methoxy group; provided that the combination, and wherein R$^1$ is methoxy group and R$^3$ and R$^4$ are methyl group is excluded.

9. The process for crystallizing as set forth in claim 8, wherein said compound is selected from the group consisting of methyl tert-butyl ketone, tert-butylbenzene, phenyltrichloromethane, carbon tetrabromide, isopropyl acetate, tert-butyl acetate, 2,2-dimethoxypropane, trimethyl orthoacetate, tetramethyl orthocarbonate, isobutyl chloride, tert-butyl chloride, 2,2-dichloropropane, 1,1,1-trichloroethane, carbon tetrachloride, 1,1,2-trichloroethane, neopentyl chloride, 2,2-dichlorobutane and bromotrichloromethane.

10. The process for crystallizing as set forth in claim 8, wherein said first solvent is replaced with a mixed solvent of said compound and auxiliary solvent for controlling crystallizing conditions.

11. The process of crystallizing as set forth in claim 8, wherein said crystallizing is first crystallization and thereafter crystallization is completed by successively adding a sufficient amount of methylcyclohexane.

12. The process for crystallizing as set forth in claim 9, wherein said first solvent is replaced with a mixed solvent of said compound and auxiliary solvent for controlling crystallizing conditions.

13. The process for crystallizing as set forth in claim 10, wherein said auxiliary solvent is selected from the group consisting of n-hexane, cyclohexane and methylcyclohexane.

14. The process for crystallizing as set forth in claim 12, wherein said auxiliary solvent is selected from the group consisting of n-hexane, cyclohexane and methylcyclohexane.

15. A process for crystallizing N$^2$-((S)-1-ethoxycarbonyl-3-phenylpropyl)-N$^6$-trifluoroacetyl-L-lysyl-L-proline, which comprises first crystallizing N$^2$-((S)-1-ethoxycarbonyl-3-phenylpropyl)-N$^6$-trifluoroacetyl-L- lysyl-L-proline wherein a sufficient amount of methyl tert-butyl ether is used as a solvent and then completing crystallization by successively adding a sufficient amount of methylcyclohexane.

16. A process for crystallizing $N^2$-((S)-1-ethoxycarbonyl-3-phenylpropyl)-$N^6$-trifluoroacetyl-L-lysyl-L-proline, which comprises providing a solution of said $N^2$-((S)-1-ethoxycarbonyl-3-phenylpropyl)-$N^6$-trifluoroacetyl-L-lysyl-L-proline in a solution with a first solvent other than methyl tert-butyl ether, replacing at least a portion of said first solvent with said methyl tert-butyl ether, first crystallizing said $N^2$-((S)-1-ethoxycarbonyl-3-phenylpropyl)-$N^6$-trifluoroacetyl-L-lysyl-L-proline from the resultant replaced solution of $N^2$-((S)-1-ethoxycarbonyl-3-phenylpropyl)-$N^6$-trifluoroacetyl-L-lysyl-L-proline, and completing crystallization by successively adding a sufficient amount of methylcyclohexane.

17. A process for crystallizing $N^2$-((S)-1-ethoxycarbonyl-3-phenylpropyl)-$N^6$-trifluoroacetyl-L-lysyl-L-proline, which comprises providing said $N^2$-((S)-1-ethoxycarbonyl-3-phenylpropyl)-$N^6$-trifluoroacetyl-L-lysyl-L-proline in a solution with a first solvent other than methyl tert-butyl ether and/or methylcyclohexane, replacing at least a portion of said first solvent with a mixed solvent of said methyl tert-butyl ether and said methylcyclohexane, and crystallizing $N^2$-((S)-1-ethoxycarbonyl-3-phenylpropyl)-$N^6$-trifluoroacetyl-L-lysyl-L-proline from the resultant replaced solution of $N^2$-((S)-1-ethoxycarbonyl-3-phenylpropyl)-$N^6$-trifluoroacetyl-L-lysyl-L-proline.

\* \* \* \* \*